US006833482B1

(12) United States Patent
Patel et al.

(10) Patent No.: US 6,833,482 B1
(45) Date of Patent: Dec. 21, 2004

(54) METHOD FOR PRODUCTION OF BIS (HYDROXY-AROMATIC)COMPOUNDS

(75) Inventors: Ben Purushotam Patel, Niskayuna, NY (US); Eric James Pressman, East Greenbush, NY (US); Ryan Christopher Mills, Mechanicville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/681,492

(22) Filed: Oct. 7, 2003

(51) Int. Cl.$^7$ ............................................... C07L 39/12
(52) U.S. Cl. ...................................................... 568/730
(58) Field of Search .......................................... 568/730

(56) References Cited

U.S. PATENT DOCUMENTS 5,177,258 A    1/1993   Becker et al.

OTHER PUBLICATIONS

M. Busch et al. in J. Prakt. Chem., *Formation of Carbon Chains in the Catalytic Reduction of Alkyl Halogen Compounds,* vol. 146, pp. 1–55 (1936) (and English abstract).
M. Busch and W. Schmidt in Chemische Berichte, *Catalytic Hydrogenation of Organic Halogen Compounds,* vol. 62, pp. 2612–2620 (1929) (and English abstract).
Abstract of JP 01–224,330 (1989).
Abstract of JP 10–299,236 (1989).
Abstract of JP 02–053,742 (1990).
Abstract of JP 62–026,238 (1987).
Abstract of JP 61–137,838 (1986).

*Primary Examiner*—Michael L. Shippen
(74) *Attorney, Agent, or Firm*—Andrew J. Caruso; Patrick K. Patnode

(57) ABSTRACT

Disclosed is a method for preparing a bis(hydroxy-aromatic) compound which comprises the steps of: contacting at least one halo-substituted hydroxy-aromatic compound in a solvent mixture comprising water and at least one organic solvent in the presence of at least one base, at least one catalyst comprising palladium and hydrogen gas at a pressure in a range of between atmospheric pressure and 350 Kilopascals.

21 Claims, No Drawings

METHOD FOR PRODUCTION OF BIS (HYDROXY-AROMATIC)COMPOUNDS

CROSS REFERENCE TO RELATED APPLICATION

This Application is related to the following U.S. Patent Application: U.S. Patent Application Ser. No. 10/680,776 entitled "PROCESS FOR THE RECOVERY OF DIHYDROXYBIARYL COMPOUNDS" being filed concurrently herewith, which is hereby incorporated herein by reference in its entirety.

BACKGROUND OF THE INVENTION

The present invention relates a method for producing bis(hydroxy-aromatic) compounds. More particularly, it relates a method for producing bis(hydroxy-aromatic) compounds in a catalytic reductive coupling reaction using hydrogen as the reductant.

Bis (hydroxy-aromatic) compounds find many uses in chemical applications, such as in dyes, plastics, pharmaceuticals and agrochemicals. In particular applications bis (hydroxy-aromatic) compounds are common monomers for use in forming polymers, such as polycarbonates, polyestercarbonates, polyesters, polyethers, polyetherimides, polyether ketones, polyetheretherketones and the like. Methods to produce bis(hydroxy-aromatic) compounds by reductive coupling of halo-substituted hydroxy-aromatic compounds are known in the art. The use of hydrogen as the stoichiometric reductant in such coupling reactions is also known. Busch et al. in Chemische Berichte, vol. 62, pp. 2612–2620 (1929) and in J. Prakt. Chem., vol. 146, pp. 1–55 (1936) describe a reductive coupling method for producing biaryl compounds from halo-substituted aromatic starting materials. The method uses high pressure hydrogen as reductant. However, halo-substituted aromatic starting materials also bearing polar substituents give lower selectivity to biaryl product. For example 4-bromophenol gives only 13% of 4,4'-dihydroxybiphenyl. Therefore, there is a continuing need for methods to synthesize bis(hydroxy-aromatic) compounds which provide high conversion of starting material and high selectivity to bis(hydroxy-aromatic) compound product.

BRIEF DESCRIPTION OF THE INVENTION

The present inventors have discovered a method to prepare bis(hydroxy-aromatic) compounds by reductive coupling of halo-substituted hydroxy-aromatic compounds using hydrogen as a reductant at low pressure. The use of low pressure hydrogen reductant provides surprisingly high levels of both starting material conversion and also selectivity to the desired bis(hydroxy-aromatic) product. The use of low pressure also conserves hydrogen reactant and obviates the need for expensive high pressure reaction equipment. The use of low pressure hydrogen reductant also allows halo-substituted hydroxy-aromatic compounds with less reactive chloro-substituents to be used as starting materials.

In one of its embodiments the present invention comprises a method for preparing a bis(hydroxy-aromatic) compound which comprises the step of: contacting at least one halo-substituted hydroxy-aromatic compound in a solvent mixture comprising water and at least one organic solvent in the presence of at least one base, at least one catalyst comprising palladium and hydrogen gas at a pressure in a range of between atmospheric pressure and 350 kilopascals Various other features, aspects, and advantages of the present invention will become more apparent with reference to the following description, examples, and appended claims.

DETAILED DESCRIPTION OF THE INVENTION

In the following specification and the claims which follow, reference will be made to a number of terms which shall be defined to have the following meanings. The singular forms "a", "an" and "the" include plural referents unless the context clearly dictates otherwise. "Optional" or "optionally" means that the subsequently described event or circumstance may or may not occur, and that the description includes instances where the event occurs and instances where it does not.

Bis(hydroxy-aromatic) compounds of the present invention are produced by catalytic reductive coupling of halo-substituted hydroxy-aromatic compounds (sometimes referred to hereinafter as starting material). Said bis (hydroxy-aromatic) compounds are attached together at the carbon atoms which formerly bore the reactive halo substituent on each hydroxy-aromatic ring of the starting material. In an illustrative example 4-halophenol produces 4,4'-dihydroxybiphenyl. More particularly, in the present context a hydroxy-aromatic compound comprises any aromatic moiety substituted on a ring carbon atom of at least one aromatic ring with a hydroxy substituent or a moiety convertible to a hydroxy substituent under the coupling reaction conditions. Suitable halo-substituted hydroxy-aromatic compounds include, but are not limited to, phenolic compounds with at least one halo substituent and optionally at least one additional substituent. In particular embodiments the halo substituents comprise iodo, bromo or chloro. In another particular embodiment the halo substituent is bromo. In yet another particular embodiment the halo substituent is chloro. The halo substituent is in a position on the aromatic ring relative to the hydroxy substituent such that catalytic reductive coupling may proceed. In particular embodiments the halo substituent is on a carbon atom on the aromatic ring adjacent to the carbon atom bearing the hydroxy substituent or separated by at least one or two carbon atoms from the carbon atom bearing the hydroxy substituent. In other particular embodiments the halo substituent is on a carbon atom on the aromatic ring separated by at least two carbon atoms from the carbon atom bearing the hydroxy substituent. Optional additional substituents comprise those which do not interfere with catalytic reductive coupling of halo-substituted hydroxy-aromatic compounds. In particular embodiments optional additional substituents comprise alkyl, aryl, ether, alkyl ether, aryl ether, carboxylic acid, carboxylic ester, an additional hydroxy substituent, and the like. Optional additional substituents may also comprise at least one other halo substituent, although in such instances it is sometimes preferred that only one halo substituent be reactive toward catalytic reductive coupling and any remaining halo substituents be less reactive either for steric or electronic reasons. Mixtures comprising more than one optional additional substituent may be present on the halo-substituted hydroxy-aromatic compound.

Bis(hydroxy-aromatic) compounds produced by the method of the present invention may be symmetrical or unsymmetrical. Symmetrical bis(hydroxy-aromatic) compounds may result from homo-coupling of two moles of the same starting material. Symmetrical bis(hydroxy-aromatic) compounds may also result from coupling of one mole of a di-halo-substituted hydroxy-aromatic compound with two moles of a mono-halo-substituted hydroxy-aromatic compound. Said di-halo-substituted hydroxy-aromatic compound comprises two reactive halogen substituents. Unsymmetrical bis(hydroxy-aromatic) compounds may result from hetero-coupling of one mole of a first halo-substituted hydroxy-aromatic compound with one mole of a second halo-substituted hydroxy-aromatic compound. In embodiments wherein more than one product could be formed, the desired product may selectively precipitate from the reaction mixture as it is formed.

The term "alkyl" as used in the various embodiments of the present invention is intended to designate both linear alkyl, branched alkyl, aralkyl, cycloalkyl, bicycloalkyl, tricycloalkyl and polycycloalkyl radicals containing carbon and hydrogen atoms, and optionally containing atoms in addition to carbon and hydrogen, for example atoms selected from Groups 15, 16 and 17 of the Periodic Table. The term "alkyl" also encompasses that alkyl portion of alkoxide groups. In various embodiments normal and branched alkyl radicals are those containing from 1 to about 32 carbon atoms, and include as illustrative non-limiting examples $C_1$–$C_{32}$ alkyl optionally substituted with one or more groups selected from $C_1$–$C_{32}$ alkyl, $C_3$–$C_{15}$ cycloalkyl or aryl; and $C_3$–$C_{15}$ cycloalkyl optionally substituted with one or more groups selected from $C_1$–$C_{32}$ alkyl. Some particular illustrative examples comprise methyl, ethyl, n-propyl, isopropyl, n-butyl, sec-butyl, tertiary-butyl, pentyl, neopentyl, hexyl, heptyl, octyl, nonyl, decyl, undecyl and dodecyl. Some illustrative non-limiting examples of cycloalkyl and bicycloalkyl radicals include cyclobutyl, cyclopentyl, cyclohexyl, methylcyclohexyl, cycloheptyl, bicycloheptyl and adamantyl. In various embodiments aralkyl radicals are those containing from 7 to about 14 carbon atoms; these include, but are not limited to, benzyl, phenylbutyl, phenylpropyl, and phenylethyl. In various embodiments aryl radicals used in the various embodiments of the present invention are those substituted or unsubstituted aryl or heteroaryl radicals containing from 6 to 18 ring carbon atoms. Some illustrative non-limiting examples of these aryl radicals include $C_6$–$C_{15}$ aryl optionally substituted with one or more groups selected from $C_1$–$C_{32}$ alkyl, $C_3$–$C_{15}$ cycloalkyl or aryl. Some particular illustrative examples of aryl radicals comprise substituted or unsubstituted phenyl, biphenyl, toluyl and naphthyl. Heteroaryl groups comprise those containing from about 3 to about 10 ring carbon atoms, and include, but are not limited to, triazinyl, pyrimidinyl, pyridinyl, furanyl, thiazolinyl and quinolinyl.

In some particular embodiments of the present invention suitable halo-substituted hydroxy-aromatic compounds comprise halo-substituted hydroxybenzene compounds with at least one additional alkyl substituent. In other particular embodiments of the present invention suitable halo-substituted hydroxy-aromatic compounds comprise halo-substituted hydroxybenzene compounds with no additional substituents. In still other particular embodiments suitable halo-substituted hydroxy-aromatic compounds comprise bromo- or chloro-substituted phenols or naphthols. In yet still another particular embodiment a suitable halo-substituted hydroxy-aromatic compound includes, but is not limited to, 2,6-dimethyl4-bromophenol, 4-bromo-1-naphthol, 4-chloro-1-naphthol, 4-bromo-ortho-alkylphenol, 4-chloro-ortho-alkylphenol, 4-bromo-ortho-cresol, 4-chloro-ortho-cresol, 4-bromophenol, 4-chloro-phenol, and the like and mixtures thereof.

The reductive coupling reaction of the present invention is performed in the presence of hydrogen gas as reductant. Although hydrogen gas is preferred, the coupling reaction may be performed alternatively in the presence of at least one reactant which generates hydrogen gas under the reaction conditions. Optionally, the hydrogen gas may be diluted with one or more inert gases such as, but not limited to, nitrogen or argon. When so diluted, the percentage of hydrogen gas present in the gas mixture is in a range of between about 40 mole % and about 99 mole %, or in a range of between about 50 mole % and about 98 mole %, or in a range of between about 60 mole % and about 98 mole %, or in a range of between about 70 mole % and about 98 mole % based on total moles gas present. Hydrogen gas may be added in any convenient manner to the reaction mixture. In one embodiment a gas comprising hydrogen is sparged through a reaction mixture at some convenient rate. In a preferred embodiment a reaction mixture is agitated under an atmosphere comprising hydrogen gas. A surprising discovery of the present invention is that hydrogen gas reductant is more effective at low pressure rather than at high pressure for both high conversion of starting material and high selectivity to desired bis(hydroxy-aromatic) product under the reaction conditions of the present invention. In particular embodiments, when the reaction is run under an atmosphere comprising hydrogen gas, the hydrogen gas is present at a pressure of less than about 350 kilopascals (kPa), or at a pressure of less than about 275 kilopascals (kPa), or at a pressure of less than about 200 kilopascals (kPa), or at a pressure of less than about 150 kPa, or at a pressure of less than about 110 kPa. In other particular embodiments the hydrogen gas is present at a pressure in a range of between about atmospheric pressure and about 200 kPa, or in a range of between about atmospheric pressure and about 150 kPa, or in a range of between atmospheric pressure and about 110 kPa. In the present context the concept of "pressure of hydrogen gas" refers to the pressure of pure hydrogen gas or to the partial pressure of hydrogen gas in a mixture with at least one other inert gas. Although the invention is in no way limited by any theory of operation, it is believed that the high selectivity to desired bis(hydroxy-aromatic) product exhibited in the present invention may be at least in part related to the decreased tendency for starting material to be reduced to the corresponding dehalogenated hydroxy-aromatic compound under high pressure hydrogen reaction conditions of the prior art.

Catalysts suitable for performing the reductive coupling reactions are those which comprise palladium. In particular embodiments of the invention suitable catalysts comprise palladium metal or any palladium compound that forms palladium metal under the reaction conditions. Palladium metal when employed as a catalyst may optionally be supported on an inert support, said support being insoluble in the reaction media Illustrative supports include, but are not limited to, carbon, alumina, barium carbonate, barium sulfate, calcium carbonate, strontium carbonate, silica and the like. The amount of palladium employed may be readily determined without undue experimentation by those skilled in the art and is generally an amount sufficient to provide high conversion of starting material and high selectivity to desired bis(hydroxy-aromatic) product under the reaction conditions. In some embodiments the amount of palladium employed is in a range of between about 0.01 wt. % and about 5 wt. %, or in a range of between about 0.05 wt. % and about 4 wt. %, or in a range of between about 0.1 wt. % and about 3 wt. %, or in a range of between about 0.5 wt. % and about 2 wt. % based on the weight of the halo-substituted hydroxy-aromatic compound.

The reductive coupling reaction of the present invention is performed in the presence of at least one base. In general the base may comprise any base of sufficient strength to neutralize hydrogen halide formed during the reductive coupling reaction. Typically, alkaline earth hydroxides or alkali metal hydroxides may be employed. At least one of sodium hydroxide or potassium hydroxide may be employed in some embodiments of the invention. Mixtures of bases are also suitable. In particular embodiments it has been surprisingly discovered that the use of potassium hydroxide results in significantly improved conversion of starting material and improved selectivity to desired bis(hydroxy-aromatic) product under the reaction conditions of the present invention.

The amount of base employed is at least sufficient to neutralize all of the hydrogen halide formed. In other embodiments of the invention the amount of base employed is at least sufficient to neutralize all of the acidic species in the reaction mixture. In still other embodiments the amount of base present is at least one molar equivalent in relation to moles of halo-substituted hydroxy-aromatic compound present. In other embodiments of the invention the base may be present in stoichiometric excess in relation to the amount of hydrogen halide that will be formed. In still other embodiments the amount of base present is at least 2 molar equivalents in relation to moles of halo-substituted hydroxy-aromatic compound present. In still other embodiments the amount of base present is less than four molar equivalents in relation to moles of halo-substituted hydroxy-aromatic compound present. In still other embodiments the amount of base present is in a range of between about 1.5 molar equivalents and about 4 molar equivalents, or in a range of between about 1.8 molar equivalents and about 4 molar equivalents, or in a range of between about 2 molar equivalents and about 4 molar equivalents in relation to moles of halo-substituted hydroxy-aromatic compound present.

A base may be added to the reaction mixture in any convenient manner. In some embodiments the base is added in pure form or in a solution comprising water. When added in pure form, solid bases may optionally be subjected to a particle size reduction step to provide higher surface area solid. When added in a solution comprising water, the base may be present in said water solution at a concentration in a range of between about 5 wt. % and about 95 wt. %, or at a concentration in a range of between about 10 wt. % and about 80 wt. %, or at a concentration in a range of between about 20 wt. % and about 70 wt. %, or at a concentration in a range of between about 40 wt. % and about 60 wt. %. In some embodiments at least a portion of base is present at the beginning of the reaction and further base is added as the reaction proceeds or at a point where a desired level of conversion of starting material has occurred. In a preferred embodiment all of the base is present at the beginning of the reaction.

The reductive coupling reaction of the present invention is performed in a solvent mixture comprising water and at least one organic solvent. In particular embodiments the solvent mixture is such that solubility of starting material is maximized. In other particular embodiments the solvent mixture is such that solubility of base is maximized. In still other particular embodiments the solvent mixture is such that solubility of both starting material and base is maximized. The ratio of water to organic solvent suitable to maximize solubility of any particular starting material or base or mixture of starting material and base may be easily determined by those skilled in the art without undue experimentation. In various embodiments of the invention suitable organic solvents comprise those which are substantially miscible with water. In the present context substantially miscible means that under the reaction conditions less than about 5 wt. % of said organic solvent is immiscible with water based on the combined weight of water and organic solvent. In some particular embodiments suitable organic solvents comprise alkyl alcohols or alkyl glycols which are substantially water-soluble. In other particular embodiments suitable organic solvents comprise methanol, ethanol, ethylene glycol and the like. Mixtures of organic solvents may also be employed.

In some embodiments of the invention the amount of organic solvent that may be present is greater than 1 wt. % or greater than 15 wt. % or greater than 20 wt. % or greater than 25 wt. % or greater than 30 wt. % or greater than 35 wt. % or greater than 40 wt. % or greater than 45 wt. % or greater than 50 wt. % based on the weight of organic solvent and water. Within this range the amount of organic solvent that may be present is less than 80 wt. % or less than 70 wt. % or less than 60 wt. % based on the weight of organic solvent and water. In other embodiments the amount of organic solvent that may be present is in a range of between about 5 wt. % and about 60 wt. %, or in a range of between about 10 wt. % and about 55 wt. %, or in a range of between about 15 wt. % and about 50 wt. %, or in a range of between about 20 wt. % and about 45 wt. %, or in a range of between about 25 wt. % and about 45 wt. %, based on the weight of organic solvent and water.

In specific embodiments the concentration of starting material in solvent mixture is in a range of between about 5 wt. % and about 50 wt. %, or in a range of between about 10 wt. % and about 45 wt. %, or in a range of between about 15 wt. % and about 35 wt. %, or in a range of between about 20 wt. % and about 30 wt. %, based on the weight of the entire reaction mixture. It will be understood that the starting material and base may be initially at least partially insoluble in the solvent mixture and will progressively dissolve in increasing amounts as the reaction proceeds and starting material and base are removed from solution.

It is to be understood that the reductive coupling reaction mixture may optionally comprise any intermediates resulting from reaction of a single reaction mixture component or of two or more components of the reaction mixture. In some particular embodiments the reductive coupling reaction mixture may optionally comprise any intermediates resulting from reaction of catalyst with at least one other reaction mixture component.

Suitable reaction temperatures for performance of catalytic reductive coupling are those temperatures which promote the coupling reaction at a reasonable rate to form bis(hydroxy-aromatic) product, and may be readily determined by those skilled in the art without undue experimentation. In particular embodiments suitable reaction temperatures are above about 45° C. In other particular embodiments suitable reaction temperatures are in the range of about 45° C. to the boiling point of the solvent media under the pressure of the reaction conditions. In still other particular embodiments suitable reaction temperatures are in the range of about 45° C. to about 100° C.; or in a range of about 55° C. to about 90° C.; or in a range of about 65° C to about 85° C.

The reductive coupling reaction may be performed in batch, semi-batch or continuous mode. The duration of the reaction is such that a desired level of bis(hydroxy-aromatic) product is formed. Suitable durations may be readily determined by those skilled in the art without undue experimentation. In some embodiments the duration of the reaction is such that there is no more conversion of starting materials or no more formation of the desired product or both. In some particular embodiments, depending upon such factors as the mass and stoichiometry of the reactants, the duration of the reaction is for about 60–120 minutes.

The course of the reaction may be monitored using known methods including, but not limited to, removal of an analytical sample and analysis by at least one of high performance liquid chromatography (HPLC), gas chromatography (GC), nuclear magnetic resonance spectroscopy (NMR), infrared spectroscopy (IR), ultraviolet spectroscopy (UV), or like methods. The course of the reaction may also be monitored in situ without removal of an analytical sample.

Following conversion to a desired level of bis(hydroxy-aromatic) product, the reaction mixture may be worked up and the bis(hydroxy-aromatic) product isolated using known methods. In one embodiment insoluble catalyst species may be removed from the reaction mixture by one or more steps of filtration, centrifugation, decantation or like methods. If desired, the catalyst may be reused, optionally following a reactivation step. Depending primarily upon the molar ratio of base to starting material, the bis(hydroxy-aromatic) compound product of the reaction may be initially formed wholly or at least partly as the bis(aromatic hydroxide) salt comprising the bis(hydroxy-aromatic) compound product and cation derived from the base. In another embodiment the reaction mixture is quenched with an acid to convert any bis(aromatic hydroxide) salt to neutral, bis(hydroxy-aromatic) product. Following removal of solvent, the bis (hydroxy-aromatic) product may optionally be purified by known methods, including, but not limited to, at least one step of crystallization, distillation, sublimation, drying or like methods. In other embodiments of the invention the bis(hydroxy-aromatic) product may be used in some subsequent process without isolation from solvent mixture.

The method of the invention provides surprisingly high levels of both starting material conversion and also selectivity to the desired bis(hydroxy-aromatic) product. In particular embodiments conversion of starting material may be greater then 20 mole %, or greater than 25 mole %, or greater than 30 mole %, or greater than 35 mole %, or greater than 40 mole %, or greater than 45 mole %, or greater than 50 mole %, or greater than 55 mole %, or greater than 60 mole %. In other particular embodiments conversion of starting material may be in a range of between about 20 mole % and about 90 mole %, or in a range of between about 25 mole % and about 90 mole %, or in a range of between about 30 mole % and about 90 mole %, or in a range of between about 35 mole % and about 90 mole %, or in a range of between about 40 mole % and about 90 mole %, or in a range of between about 45 mole % and about 90 mole %, or in a range of between about 50 mole % and about 90 mole %, or in a range of between about 55 mole % and about 90 mole %. In particular embodiments the selectivity to the desired bis(hydroxy-aromatic) product may be greater then 20 mole %, or greater than 25 mole %, or greater than 30 mole %, or greater than 35 mole %, or greater than 40 mole %, or greater than 45 mole %, or greater than 50 mole %, or greater than 55 mole %, or greater than 60 mole %. In other particular embodiments the selectivity to the desired bis(hydroxy-aromatic) product may be in a range of between about 20 mole % and about 90 mole %, or in a range of between about 25 mole % and about 90 mole %, or in a range of between about 30 mole % and about 90 mole %, or in a range of between about 35 mole % and about 90 mole %, or in a range of between about 40 mole % and about 90 mole %, or in a range of between about 45 mole % and about 90 mole %, or in a range of between about 50 mole % and about 90 mole %, or in a range of between about 55 mole % and about 90 mole %.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES 1–22 AND COMPARATIVE EXAMPLES 1–2

General Experimental procedure: In a typical batch experiment, sixteen 3-dram vials containing stir bars were charged with 1 mole percent palladium based on moles 4-bromophenol starting material (added as 5% palladium on carbon), water, optionally an organic solvent and 4-bromophenol as shown in Table 1. Then the vials were loaded into an aluminum block which was suspended in a 1-gallon Parr autoclave reactor. After the reactor was sealed, the head space of the reactor was typically flushed with hydrogen gas and then pressurized to a given pressure with hydrogen gas. Comparative Examples (C.Ex.) 1 and 2 were pressurized to high pressure. The reactor was then heated to a temperature of 75° C., and stirred for 90 minutes. After the reaction was complete, the reactor was typically cooled to room temperature and depressurized. From each of the sixteen vials an aliquot of known mass was taken and worked up using standard procedures for BPLC analysis of unreacted starting material, 4,4'-dihydroxybiphenyl, and phenol. The analytical results are shown in Table 1. The term "equivalents of base" refers to molar equivalents relative to 4-bromophenol. The values for wt. % solvent refer to weight percent relative to the weight of the water/organic solvent combination.

TABLE 1

| Experiment No. | Base | Equivalents of base | Solvent | Wt. % solvent | $H_2$ Pressure (kPa) | Wt. % 4-bromophenol | % Conversion | % Selectivity for 4,4'-dihydroxybiphenyl |
|---|---|---|---|---|---|---|---|---|
| C. Ex. 1 | NaOH | 1 | methanol | 33 | 1723 | 33 | 55 | 5 |
| C. Ex. 2 | NaOH | 2 | methanol | 33 | 1723 | 33 | 72 | 17 |
| Ex. 1 | NaOH | 0.5 | methanol | 24 | 103 | 33 | 17 | 36 |
| Ex. 2 | NaOH | 1 | methanol | 33 | 103 | 33 | 45 | 47 |
| Ex. 3 | NaOH | 2 | methanol | 41 | 103 | 33 | 63 | 50 |
| Ex. 4 | KOH | 0.5 | methanol | 21 | 103 | 30 | 6 | 30 |
| Ex. 5 | KOH | 1 | methanol | 30 | 103 | 30 | 19 | 65 |
| Ex. 6 | KOH | 2 | methanol | 43 | 103 | 30 | 29 | 70 |
| Ex. 7 | NaOH | 2 | iso-propanol | 33 | 103 | 33 | 20 | 9 |
| Ex. 8 | NaOH | 2 | ethanol | 33 | 103 | 33 | 12 | 3 |

TABLE 1-continued

| Experiment No. | Base | Equivalents of base | Solvent | Wt. % solvent | H₂ Pressure (kPa) | Wt. % 4-bromophenol | % Conversion | % Selectivity for 4,4'-dihydroxybiphenyl |
|---|---|---|---|---|---|---|---|---|
| Ex. 9 | NaOH | 2 | methanol | 33 | 103 | 33 | 81 | 43 |
| Ex. 10 | NaOH | 2 | sulfolane | 33 | 103 | 33 | 7 | 12 |
| Ex. 11 | KOH | 2 | iso-propanol | 30 | 103 | 30 | 9 | 21 |
| Ex. 12 | KOH | 2 | ethanol | 30 | 103 | 30 | 3 | 11 |
| Ex. 13 | KOH | 2 | methanol | 30 | 103 | 30 | 41 | 68 |
| Ex. 14 | KOH | 2 | sulfolane | 30 | 103 | 30 | 5 | 19 |
| Ex. 15 | NaOH | 2 | — | 0 | 103 | 29 | 56 | 2 |
| Ex. 16 | NaOH | 2 | methanol | 15 | 103 | 29 | 28 | 40 |
| Ex. 17 | NaOH | 2 | methanol | 28 | 103 | 29 | 17 | 54 |
| Ex. 18 | NaOH | 2 | methanol | 42 | 103 | 29 | 19 | 49 |
| Ex. 19 | KOH | 2 | — | 0 | 103 | 29 | 29 | 12 |
| Ex. 20 | KOH | 2 | methanol | 15 | 103 | 29 | 40 | 63 |
| Ex. 21 | KOH | 2 | methanol | 29 | 103 | 29 | 58 | 67 |
| Ex. 22 | KOH | 2 | methanol | 37 | 103 | 25 | 55 | 65 |

Comparative Experiments 1 and 2 show that reactions run under high pressure of hydrogen provide high conversion of 4-bromophenol starting material but low selectivity to the desired 4,4'-dihydroxybiphenyl product. In contrast Examples 2 and 3 of the invention run under conditions similar to those of Comparative Examples 1 and 2 but at low hydrogen pressure provide high conversion of 4bromophenol starting material and also surprisingly higher selectivity to the desired 4,4'-dihydroxybiphenyl product compared to the Comparative Examples. Examples wherein potassium hydroxide was used in place of sodium hydroxide show surprisingly higher selectivity for 4,4'-dihydroxybiphenyl product in various organic solvent-water mixtures (compare Examples 11–14 with Examples 7–10). Examples wherein potassium hydroxide was used in place of sodium hydroxide also show both surprisingly higher conversion of starting material and higher selectivity for 4,4'-dihydroxybiphenyl product in methanol-water solvent mixtures (compare Examples 20–22 with Examples 16–18). Examples 4–6 show that the increase in selectivity for 4,4'-dihydroxybiphenyl begins to level off at some concentration of potassium hydroxide above about 1 equivalent. Examples wherein a methanol-water mixture was used show surprisingly higher selectivity for 4,4'-dihydroxybiphenyl product than do similar Examples wherein water alone was employed as solvent, no matter what base is employed, as seen in comparing Example 15 with Examples 16–18 and also in comparing Example 19 with Examples 20–22.

EXAMPLE 23

A reductive coupling reaction is performed under the same conditions as described for Example 21 using the same reaction mixture components except that hydrogen gas is diluted with an inert gas such as argon or nitrogen such that the mole % of hydrogen present is in a range of between about 40 mole % and about 99 mole %, based on total moles gas present and the partial pressure of hydrogen gas is 103 kPa. The conversion of starting material and selectivity for 4,4'-dihydroxybiphenyl product is higher than that obtained when the partial pressure of hydrogen gas in the reaction mixture is 1723 kPa.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All Patents cited herein are incorporated herein by reference.

What is claimed is:

1. A method for preparing a bis(hydroxy-aromatic) compound which comprises the step of: contacting at least one halo-substituted hydroxy-aromatic compound in a solvent mixture comprising water and at least one organic solvent in the presence of at least one base, at least one catalyst comprising palladium and hydrogen gas at a pressure in a range of between atmospheric pressure and 350 kilopascals.

2. The method of claim 1 wherein the halo-substituted hydroxy-aromatic compound is selected from the group consisting of bromo-substituted hydroxy-aromatic compounds, chloro-substituted hydroxy-aromatic compounds and mixtures thereof.

3. The method of claim 1 wherein the halo-substituted hydroxy-aromatic compound is additionally substituted with at least one substituent selected from the group consisting of alkyl, aryl, ether, alkyl ether, aryl ether, alkyl alcohol, carboxylic acid, carboxylic ester, an additional hydroxy substituent, an additional halogen substituent and mixtures thereof.

4. The method of claim 1 wherein the halo-substituted hydroxy-aromatic compound is selected from the group consisting of 4-bromo-1-naphthol, 4chloro-1-naphthol, 4-bromo-ortho-alkylphenol, 4-chloro-ortho-alkylphenol, 4-bromo-ortho-cresol, 4-chloro-ortho-cresol, 4-bromophenol and 4-chloro-phenol.

5. The method of claim 1 wherein the organic solvent is present in an amount in a range of between greater than 1 wt. % and less than 80 wt. % based on the weight of organic solvent and water.

6. The method of claim 1 wherein the organic solvent is present in an amount in a range of between about 20 wt. % and about 45 wt. % based on the weight of organic solvent and water.

7. The method of claim 1 wherein the organic solvent is substantially soluble in water.

8. The method of claim 1 wherein the organic solvent is selected from the group consisting of alkyl alcohols, alkyl glycols and mixtures thereof.

9. The method of claim 1 wherein the organic solvent is selected from the group consisting of methanol, ethanol, ethylene glycol and mixtures thereof.

10. The method of claim 1 wherein the halo-substituted hydroxy-aromatic compound is present in the solvent mixture at a concentration of between about 5 wt. % and about 50 wt. % based on the weight of the entire reaction mixture.

11. The method of claim 1 wherein the base is selected from the group consisting of alkaline earth metal hydroxides, alkali metal hydroxides and mixtures thereof.

12. The method of claim 11 wherein the base is selected from the group consisting of sodium hydroxide and potassium hydroxide.

13. The method of claim 1 wherein the base is present at a level of at least one molar equivalent in relation to moles of the halo-substituted hydroxy-aromatic compound.

14. The method of claim 1 wherein the base is present in stoichiometric excess in relation to moles of the halo-substituted hydroxy-aromatic compound.

15. The method of claim 14 wherein the base is present at a level in a range of between about 1.8 molar equivalents and about 4 molar equivalents in relation to moles of the halo-substituted hydroxy-aromatic compound.

16. The method of claim 1 wherein the catalyst comprises palladium metal and an inert support.

17. The method of claim 1 wherein the catalyst is present at a level in a range of between about 0.05 wt. % and about 4 wt. % based on the weight of the halo-substituted hydroxy-aromatic compound.

18. The method of claim 1 wherein hydrogen gas is at a pressure of less than about 200 kilopascals.

19. The method of claim 1 wherein hydrogen gas is at a pressure of less than about 150 kilopascals.

20. The method of claim 1 wherein hydrogen gas is at a pressure of less than about 110 kilopascals.

21. A method for preparing a bis(hydroxy-aromatic) compound which comprises the step of: contacting at least one halo-substituted hydroxy-aromatic compound selected from the group consisting of 4-bromo-ortho-alkylphenol, 4-chloro-ortho-alkylphenol, 4-bromo-ortho-cresol, 4-chloro-ortho-cresol, 4-bromophenol and 4-chloro-phenol, in a solvent mixture comprising water and 20–45 wt. % methanol based on the weight of methanol and water, in the presence of potassium hydroxide, at least one catalyst comprising palladium and hydrogen gas at a pressure in a range of between atmospheric pressure and 350 kilopascals.

* * * * *